(12) United States Patent
Friel

(10) Patent No.: US 8,303,746 B2
(45) Date of Patent: Nov. 6, 2012

(54) OCULAR PROSTHESIS AND FABRICATION METHOD OF SAME

(76) Inventor: Timothy P. Friel, Rockville, MD (US)

( * ) Notice: Subject to any disclaimer, the term of this patent is extended or adjusted under 35 U.S.C. 154(b) by 886 days.

(21) Appl. No.: 11/344,115

(22) Filed: Feb. 1, 2006

(65) Prior Publication Data

US 2006/0173541 A1    Aug. 3, 2006

Related U.S. Application Data

(60) Provisional application No. 60/649,020, filed on Feb. 1, 2005.

(51) Int. Cl.
*B32B 27/00* (2006.01)
*B29D 11/02* (2006.01)

(52) U.S. Cl. ......... 156/242; 264/401; 623/4.1; 623/6.64

(58) Field of Classification Search ............... 623/6.64, 623/4.1; B29D 11/02
See application file for complete search history.

(56) References Cited

U.S. PATENT DOCUMENTS

| | | | | |
|---|---|---|---|---|
| 2,467,401 A * | 4/1949 | Murphey et al. | ............ | 623/6.64 |
| 2,551,781 A * | 5/1951 | Yuhas | ............ | 623/6.64 |
| 2,563,462 A * | 8/1951 | Galeski | ............ | 623/6.64 |
| 2,580,583 A * | 1/1952 | Noelle | ............ | 623/6.64 |
| 2,603,792 A * | 7/1952 | Jardon et al. | ............ | 623/6.64 |
| 3,480,971 A * | 12/1969 | Smith | ............ | 623/6.64 |
| 4,332,039 A | 6/1982 | LaFuente | | |
| 5,026,392 A * | 6/1991 | Gordon | ............ | 623/6.64 |
| 5,061,279 A | 10/1991 | Friel | | |
| 5,171,265 A | 12/1992 | Kelley | | |
| 5,326,346 A * | 7/1994 | Cortes | ............ | 623/6.64 |
| 5,334,172 A | 8/1994 | Kelley | | |
| 5,487,012 A * | 1/1996 | Topholm et al. | ............ | 700/163 |
| 5,733,333 A * | 3/1998 | Sankey | ............ | 623/4.1 |
| 5,741,215 A * | 4/1998 | D'Urso | ............ | 600/407 |
| 5,742,172 A | 4/1998 | Yasutake | | |
| 5,876,435 A | 3/1999 | Swords et al. | | |
| 6,025,114 A * | 2/2000 | Popat et al. | ............ | 430/284.1 |
| 6,139,577 A * | 10/2000 | Schleipman et al. | ............ | 623/6.64 |

(Continued)

FOREIGN PATENT DOCUMENTS

GB    2219212 A  * 12/1989

OTHER PUBLICATIONS

McGurk, M., A.A. Amis, P. Potamianos, and N.M. Goodger, "Rapid prototyping techniques for anatomical modeling in medicine", Annals of the Royal College of Surgeons of England, vol. 79, No. 3, May 1997, pp. 169-174.*

(Continued)

*Primary Examiner* — William Bell
(74) *Attorney, Agent, or Firm* — Oblon, Spivak, McClelland, Maier & Neustadt, L.L.P.

(57) ABSTRACT

An ocular prosthesis includes a posterior sclera portion partially nested with an anterior clear portion. An iris disk piece and/or a retinal chip may also be disposed between the posterior and anterior portions. A method for manufacturing the ocular prosthesis includes scanning an impression of an eye socket or an existing ocular prosthesis, fabricating posterior and anterior portions from geometrical models generated from the scans, and forming the ocular prosthesis by joining the two portions. In another embodiment of the method, a photograph of an iris is provided and manipulated to form a multi disk iris piece to be used in the ocular prosthesis.

22 Claims, 14 Drawing Sheets

U.S. PATENT DOCUMENTS

| | | | |
|---|---|---|---|
| 6,187,041 B1 | 2/2001 | Garonzik | |
| 6,346,121 B1 | 2/2002 | Hicks et al. | |
| 6,391,057 B1 | 5/2002 | Schleipman et al. | |
| 6,427,087 B1 | 7/2002 | Chow et al. | |
| 6,530,953 B2 | 3/2003 | Garonzik | |
| 6,532,299 B1 * | 3/2003 | Sachdeva et al. | 382/128 |
| 6,576,013 B1 | 6/2003 | Budman et al. | |
| 2002/0080327 A1 * | 6/2002 | Clark et al. | 351/162 |
| 2003/0219148 A1 * | 11/2003 | Scharlack et al. | 382/128 |
| 2004/0005374 A1 | 1/2004 | Narang et al. | |
| 2004/0077279 A1 | 4/2004 | Lam et al. | |
| 2004/0113301 A1 | 6/2004 | Burger et al. | |
| 2004/0118924 A1 | 6/2004 | Gurevich et al. | |
| 2004/0156554 A1 | 8/2004 | McIntyre | |
| 2004/0247428 A1 | 12/2004 | Gotta et al. | |
| 2004/0265770 A1 | 12/2004 | Chapoulaud et al. | |
| 2005/0010450 A1 | 1/2005 | Hultgren et al. | |
| 2005/0275137 A1 * | 12/2005 | Stolpe et al. | 264/294 |

OTHER PUBLICATIONS

Cadalyst, "On the Job: Technology Makes More Time for the Human Touch", Nov. 15, 2004, 3 pages, available at http://www.cadalyst.com/manufacturing/on-job-technology-makes-more-time-human-touch-10309.*

Roland DGA Corporation Technical Literature for LPX-1200 3D Laser Scanner, Jan. 23, 2005, available at http://web.archive.org/web/20051230143636/rolanddga.com/products/3D/scanners/LPX-1200/default.asp?t=2, 2 pages.*

* cited by examiner

OCULAR PROSTHESIS AND FABRICATION METHOD OF SAME

CROSS-REFERENCE TO RELATED APPLICATIONS

This application claims the benefit of U.S. Provisional Application No. 60/649,020, filed on Feb. 1, 2005. The content of which is incorporated herein by reference in its entirety.

BACKGROUND OF THE INVENTION

1. Field of the Invention

The invention relates in general to a prosthetic eye and, more particularly, to an ocular prosthesis and a process of fabrication of the same.

2. Description of the Related Art

It is not uncommon for a person to have a natural eye removed because of a severe trauma, a congenital abnormality, or a disease, such as, for example, an infection, the presence of a tumor, or untreatable painful glaucoma. In these situations, the natural eye is removed by an acceptable medical procedure, for example, by enucleation or evisceration, during which a orbital implant is surgically implanted to replace lost orbital volume. It is also not uncommon for a person to have a smaller than normal, or phthisical eye, that is blind. In order to restore the person to a more normal anatomical structure and restore the cosmetic defect created by these conditions an ocular prosthesis is created. The initial step in creating this prosthesis is the taking of an impression of the ocular socket. From that impression, an ocular prosthesis simulating the person's natural eye is created and inserted into the ocular socket posterior to the lids and anterior to the orbital implant or phthisical globe. With such a procedure, a person's psychological trauma associated with the eye loss is reduced, and a more cosmetically acceptable appearance results from the use of the prosthesis. FIG. 1 illustrates a generic ocular prosthesis 10. As shown, these prostheses usually comprise a scleral region 20 with veins 30, an iris 40, a pupil 50 and a clear corneal layer (not illustrated).

Although several improvements have been reported in the general art of ocular prosthesis, fabrication methods currently used are based upon outdated technology, are cumbersome, lack a high degree of precision, and are time consuming, as further explained below. Examples of improvements in the art include a method of magnetically coupling a prosthesis with an ocular implant described by Garonzik in U.S. Pat. No. 6,530,953 designed to eliminate the use of a coupling post in the integration process of the prosthesis with the ocular implant. Kelley, in U.S. Pat. No. 5,171,265, discloses a self-lubricating ocular prosthesis designed to dispense a lubricating fluid by use of a dispensing ball or a button that can be depressed on demand. U.S. Pat. No. 4,332,039, issued on Jun. 1, 1982 to Henry LaFuente, discloses an ocular prosthesis having a pupil that changes in diameter to simulate the behavior of a natural eye when exposed to light of varying intensity. The U.S. Patent to Schleipman et al. (U.S. Pat. No. 6,391,057) discloses a prosthesis with similar characteristics to the one disclosed by LaFuente; while Friel, in U.S. Pat. No. 5,061,279, disclosed an ocular prosthesis capable of simulating human pupil dilation by the use of photochromic pigments that changes the density of their color in response to differing wavelengths of light from clear to opaque. Finally, in U.S. Pat. No. 5,326,346, Cortes discloses an ocular prosthesis made of light-cured urethane dimethacrylate, thus minimizing allergic reactions by the user of the prosthesis by essentially eliminating any residual monomers.

However, despite the above-noted exemplary improvements, conventional fabrication methods produce ocular prosthetics whose shapes are usually inaccurate and difficult to reproduce, are time consuming, employ materials and methods of curing the materials that have the potential to cause undesirable allergic reactions, and are labor intensive.

Conventional processes that are currently used to produce ocular prosthetics have been around for more than sixty years. They traditionally begin with the taking of an impression of the anophthalmic or enophthalmic eye socket in a process similar to that of taking a dental impression. First a conforming impression tray is selected and placed into the socket anterior to the globe or implant and posterior to the lids. An impression material is then introduced into the eye socket via a tube protruding from the anterior surface of the impression tray and projecting out between the lids by means of a syringe connected to the tube. After the impression material has set, the impression is removed and invested in dental gypsum in order to obtain a positive cast of the posterior aspect of the eye socket.

Subsequently, the gypsum cast is coated with a separating medium and either dental base plate wax or inlay wax is then shaped thereon in an empirical approximation of the anterior curves of the wax form that will comprise the form for investment. These anterior curves and the posterior surface of the wax are modified in order to achieve patient comfort, appropriate anterior/posterior dimension, palpebral fissure curvature, and iris center position. The iris center position is then identified with a screw coated in wax or an iris peg that identifies the iris center and plane. Because of the empirical nature of this portion of the conventional fabrication processes, an undesirable variation in the accuracy of the shape occurs.

Once the wax investment form is finished, a two part mold is made of the prototype ocular prosthesis using dental gypsum within a stainless steel or brass flask. The anterior portion of the mold is invested, a separating medium is applied, and the posterior portion of the mold is invested. After the mold sections have set, the flask is opened and the wax form and iris center are removed from the mold.

In the most common form of iris duplication, the iris is painted using a viscous monomer-polymer solution and dry artist's pigments onto a Poly Methyl Methacrylate Acrylic, or PMMA disc. A PMMA corneal-pupil piece (CPP) that approximates the clear cornea is then adhered to the painted surface with a viscous monomer-polymer solution. In other forms of the process, the iris is painted on a thin sheet of tin foil placed over the convex side of a steel die which is then cured with PMMA in order to form the CCP, or the iris is painted in the appropriate location on a slightly convex anterior surface of the white portion of the prosthesis. The problems associated with hand painted irises include the inherent inaccuracy of hand painting and the fact that only a limited three-dimensional depth effect can be portrayed.

When forming the white posterior section of the prosthesis, the above-summarized, two-part mold is cleaned and inspected and a liquid separator is applied to each gypsum section. The corneal-pupil-iris piece (CPIP) is then placed into its pre-determined location in the mold anterior section. PMMA powder that has had intrinsic pigments added in order to replicate the base colors of the natural sclera of the eye is then mixed with PMMA monomer. This mixture is allowed to polymerize until it reaches a consistency that pulls apart with a snap. The polymerized scleral acrylic mixture is packed into the anterior mold section to overflow and the posterior section of the mold is then placed onto the anterior portion thereof. The mold is then placed in a mechanical or hydraulic press and the excess PMMA is pressed out and the mold is then placed in a curing device and heat alone or heat and or pressure are applied until polymerization has been completed. Because the amount of undesirable monomers that may remain in the prosthesis, the curing process requires long curing times. It is also not practical to destructively test the material once cured in order to ensure proper polymerization as the batch size is necessarily small, then the prosthesis itself would be destroyed. After curing, the scleral portion of the prosthesis is removed from the mould, parting line flash is ground away, the corneal area is reduced until the iris is exposed to a desired diameter, and the anterior-posterior surface of the scleral area is reduced by hand.

Subsequently, iris tones are next enhanced over the CPIP, or applied to the anterior surface. The colors of the sclera are duplicated on the surface and silk fibers are added to duplicate the veining patterns of the contra-lateral eye. The prosthesis is then placed in a drying oven to prepare it for the placement of a clear acrylic over the anterior surface. The mold is again inspected, repaired, and a liquid separator is applied to both gypsum sections in preparation for the application of a clear capping. Clear PMMA polymer and monomer are mixed and polymerized until reaching the same snappy state as previously described. The clear acrylic is then placed on the anterior surface of the painted section and the anterior and posterior flask sections are closed and the excess acrylic is pressed out. Polymerization and cooling as previously described follow. The same material concerns as previously described apply to this process of polymerization.

Finally, the prosthesis is removed from the mold, parting line flash and surface irregularities caused by latent air bubbles or other defects in the mould are then ground away, and the surfaces are smoothed with a fine hand piece burr. The prosthesis is then smoothed with a paste of medium flour of pumice and water. Progressively finer abrasives are used until all surfaces are smooth and show no scratches under ten times magnification. The prosthesis is given a final inspection, is cleaned and disinfected and prepared for delivery to the patient.

Based at least on the foregoing summarized discussion and the exemplary problems identified with conventional methods to fabricate ocular prostheses, a need exists for an advanced ocular prosthesis and an advanced method of fabrication of an ocular prosthesis having several unique capabilities, including, as non-limiting examples: (1) improved shape accuracy through the use of both the anterior and posterior aspects of the initial impression of the ocular socket; (2) allowance for accurate and repeatable shape modification; (3) elimination of several fabrication steps by providing a way for the retention of a computerized record of an accurate shape of the ocular prosthesis; 4) use of materials that contain no methyl methacrylate monomer, or that have been tested in a manufacturing facility and proven to contain only acceptably low levels of methyl methacrylate monomer, thus possibly reducing the potential for patient allergic reactions; (5) reduction in the time necessary to create the final product; (6) automation of what has in the past been a "hand made" technique, as just explained; (7) a more realistic portray of a person's natural iris; and (8) allowance for the placement in the prosthesis of advanced technology devices, such as a retinal chip, in view of the precise ability to machine the ocular prosthesis.

SUMMARY OF THE INVENTION

An ocular prosthesis is disclosed with a posterior sclera portion, an iris disk disposed on a front surface of the posterior sclera portion, and an anterior clear portion covering the front surface of the posterior sclera portion and the iris disk. In another embodiment, the ocular prosthesis has a posterior sclera portion and an anterior clear portion, a back surface of the anterior clear portion being partially nested with a front surface of the posterior sclera portion.

A method of manufacturing an ocular prosthesis is also disclosed including the steps of providing an impression of an eye socket or an existing ocular prosthesis, scanning the impression or the existing ocular prosthesis, fabricating a posterior scleral portion and an anterior clear portion based on scans produced by the scanning of the impression or the existing ocular prosthesis, and forming the ocular prosthesis by joining the fabricated posterior sclera portion to the anterior clear portion. In another embodiment of the fabrication method, an ocular prosthesis is fabricated by providing an impression of an eye socket and an iris photograph, scanning the impression of the eye socket, fabricating a posterior sclera portion and an anterior clear portion based on scans produced by the scanning of the impression of the eye socket, forming an iris disk from the iris photograph, disposing the iris disk on the fabricated posterior sclera portion, and forming the ocular prosthesis by joining the fabricated posterior sclera portion containing the iris disk to the anterior clear portion.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining several preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
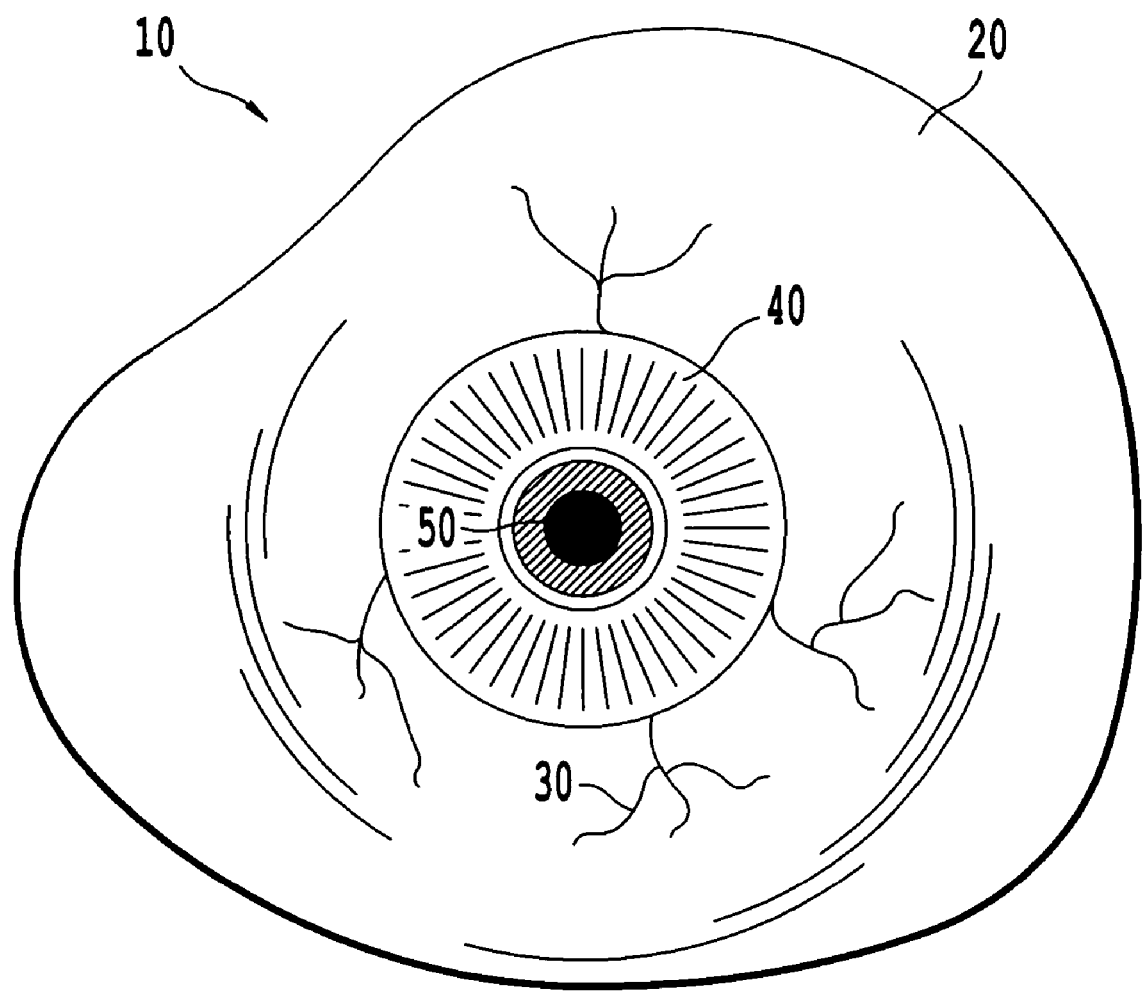
FIG. 1 illustrates a generic ocular prosthesis showing the main components thereof.
Figure 2A:
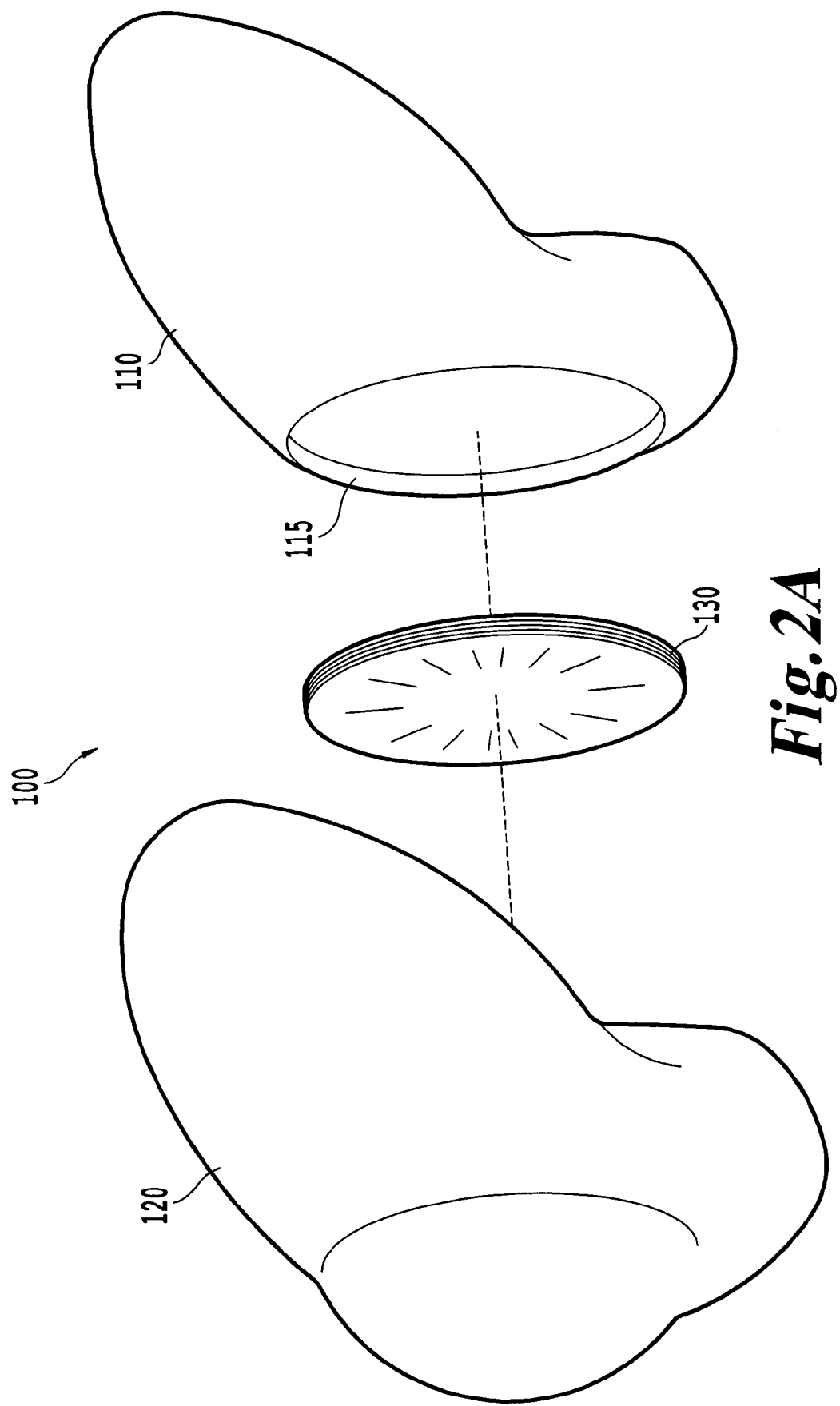
FIGS. 2A-2D illustrate a first embodiment of an ocular prosthesis according to the invention.
Figure 2B:
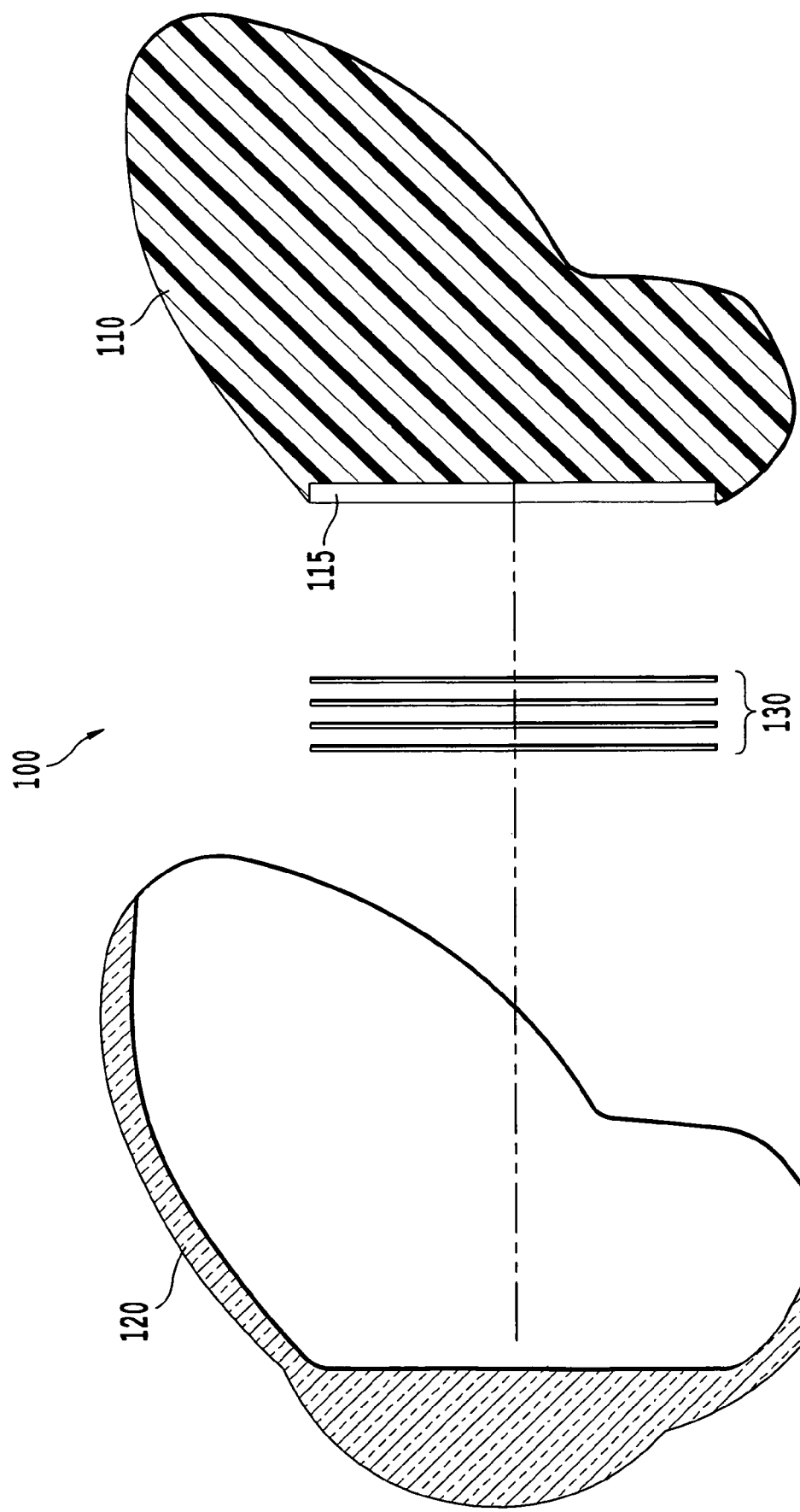
Figure 2C:
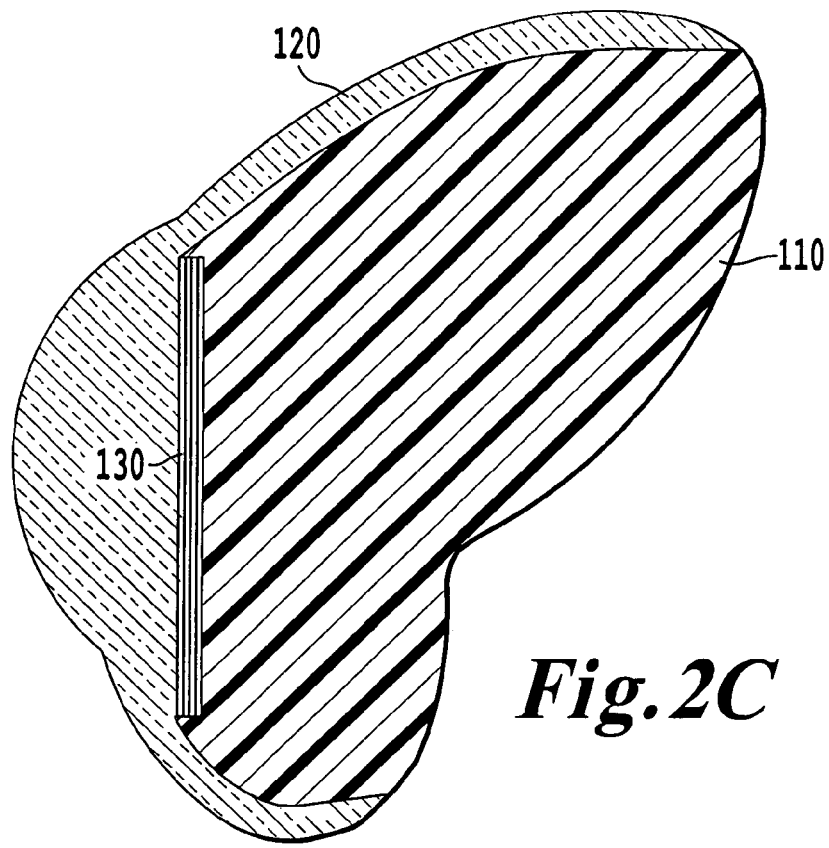

Referring now to the drawings, wherein like reference numerals designate identical or corresponding parts throughout the several views, one of the embodiments of the ocular prosthesis of the invention will be described. FIG. 2 illustrates an embodiment of the ocular prosthesis 100 according to the invention. FIG. 2A is an exploded view of the main components; FIGS. 2B and 2C are cross-section views of the prosthesis of FIG. 2A with separated and assembled components, respectively; and FIG. 2D illustrates details of the iris piece of the prosthesis.

As illustrated in FIG. 2A, the main components of the ocular prosthesis 100 are the posterior portion 110 that simulates the natural sclera of the eye, an iris piece 130, and an anterior clear portion 120 that simulates the natural corneal and external surfaces of the eye. As illustrated, the posterior portion 110 includes a circular depression, or iris table 115 configured to accommodate the iris piece 130 therein. The depression 115 has a depth and diameter substantially the same as the thickness and diameter of the iris piece 130. As later further explained, the anterior surface of the posterior portion 110 is painted using dry artists pigment mixed with a light cure adhesive to match the colors of the patient's corresponding eye. Silk fibers that simulate the veining patterns of the eye are also placed on the anterior surface and coated with an adhesive to duplicate the patient's natural vein pattern.

Figure 2D:
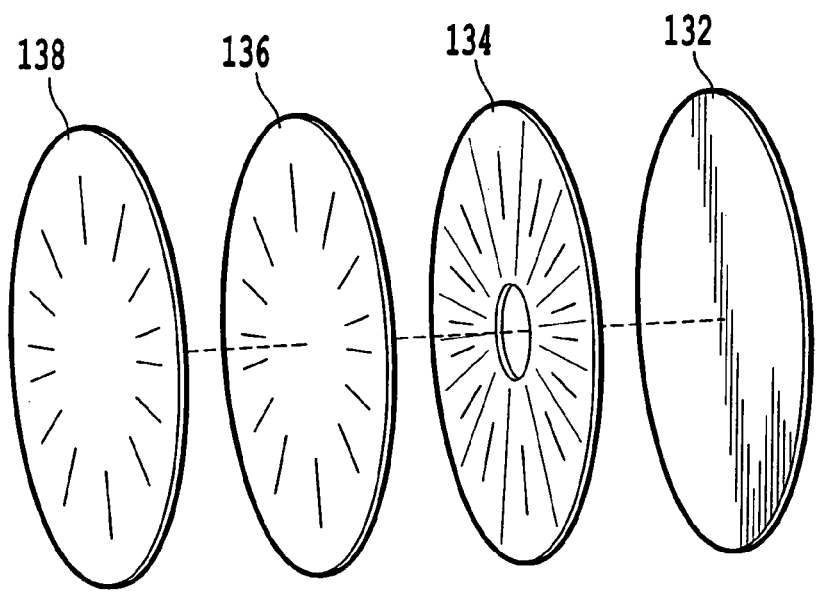

As illustrated in FIGS. 2B and 2D, the iris piece 130 is composed of a plurality of layers, including a dark almost black pupil layer 132 printed on photographic paper, a base iris color layer 134 printed on photographic paper and cut along the exterior edge of the iris so as to have the appropriate iris diameter, and having a hole of the appropriate diameter for the pupil cut out of the center, and several lighter layers of color 136, 138 that have been subtracted out from the base photograph and printed on a clear transparency film as later further explained The layers 132-138 of the iris piece 130 are then placed using light cure adhesive into the circular depression 115 of the posterior portion 110 and the anterior (120) and posterior (110) components of the prosthesis are joined together and bonded using a light-cured adhesive and an ultraviolet light source. Those of ordinary skill in the applicable arts will appreciate that another embodiment of the invention just described could comprise an ocular prosthesis that uses the advantageous posterior and anterior portions with and iris and other elements, such as veins, painted on the posterior portions.

Figure 3:
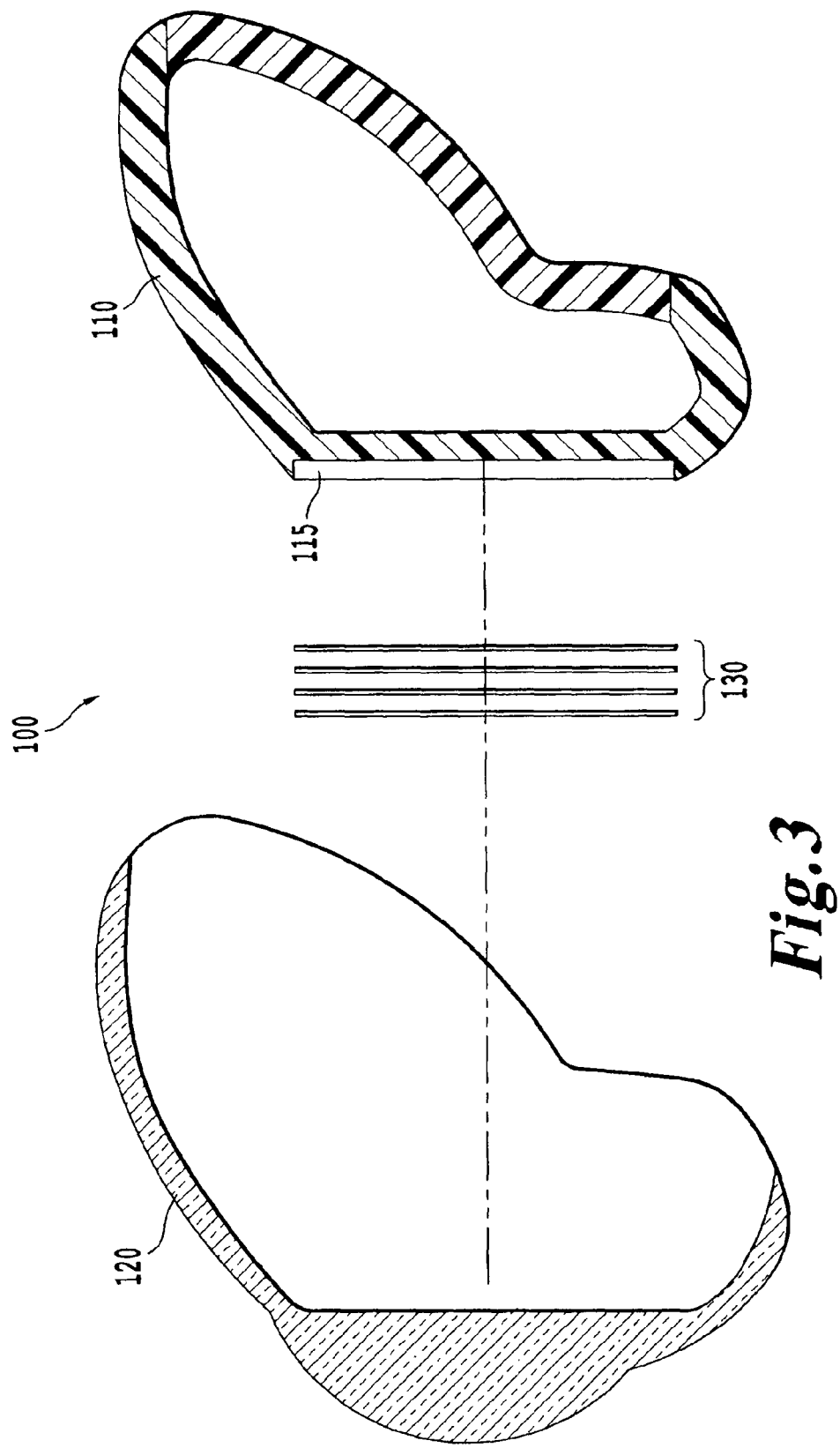
FIG. 3 illustrates a second embodiment of an ocular prosthesis according to the invention.

In another embodiment of the invention, as shown in FIG. 3, the posterior portion 110 may be made hollow. One of the advantageous features of this embodiment is that the weight of the final ocular prosthesis may be reduced, thus reducing the effects of gravity on the lower eyelid of the patient.

Figure 4:
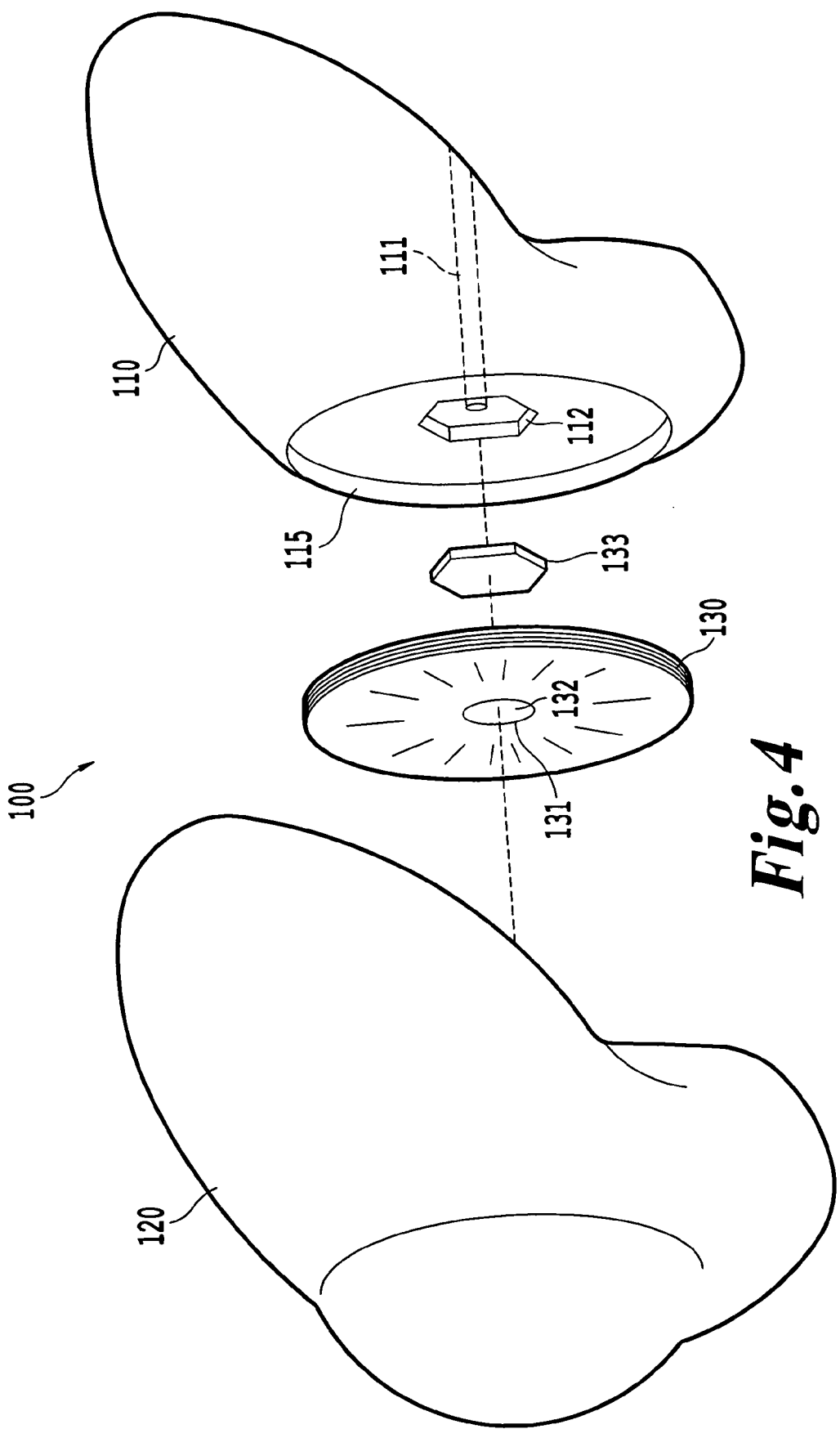
FIG. 4 illustrates a third embodiment of an ocular prosthesis according to the invention.

FIG. 4 illustrates yet another embodiment of the ocular prosthesis 100 according to the invention. In this embodiment, a depression 112 may be created in the center of the iris depression 115 in the posterior portion 110 so as to create a space for the insertion of a retinal chip 133 or other similar devices design to improve the sight of a person with sight disability. These advanced devices have been previously described and will not be repeated here. See, for example, U.S. Pat. No. 6,427,087 issued to Chow et al. on Jul. 30, 2002 (the entire contents of which are incorporated herein by reference).

It should be understood that the retinal chip is provided as a non-limiting example of an image capture device for the transformation of a visual image from light energy to electrical energy and the transmission either directly or indirectly to the optic nerve or other neural tissue. Those of ordinary skill in the art will understand that such a process may vary according to the hardware used and still be within the scope of the instant invention. A passage 111 (FIG. 4) may also be provided in the posterior portion 110 in order to provide a space for the placement of a cable or other means of transmission of the signal from the retinal chip 133 to the posterior portion 110 of the prosthesis 100 where it can then be connected or transferred to another cable or means of transmission to the remnant of the persons optic nerve or other neural tissues.

As shown in FIG. 4, the iris disk 130 in this embodiment may be perforated with a hole 131 so as to allow outside light to enter and reach the retinal chip. In addition, a light collecting lens 132 may also be used so as to increase the efficiency of the light collecting process for better performance of the retinal chip.

Figure 5:
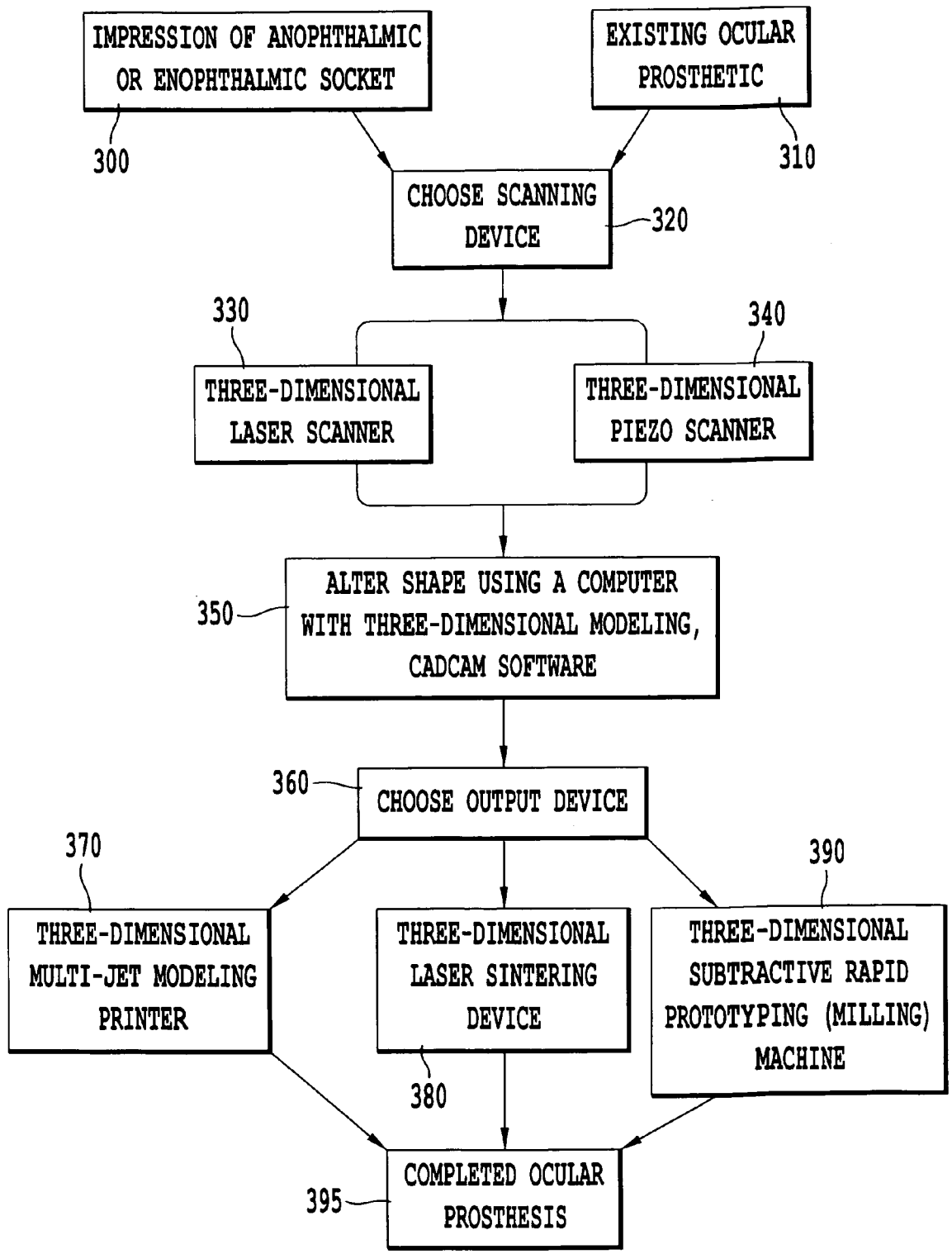
FIG. 5 is a flowchart illustrating a first embodiment for an ocular prosthesis fabrication method according to the invention.

FIG. 5 is a flowchart illustrating a first embodiment for an ocular prosthesis fabrication method according to the invention. As illustrated, an impression of the anophthalmic or enophthalmic socket at 300 or a patient's existing ocular prosthesis at 310 is provided and placed into a three dimensional scanning device at 320.

The impression taken of the patient's anophthalmic or enophthalmic socket is done in a manner that is well known to an ocularist, as already described. In summary, the process includes the placement of an impression tray (similar to a dental impression tray, but of an appropriate shape for the ocular socket) into the patient's orbit and injecting an alginate, Polyvinylsiloxane, or other dental type impression material into the socket. This material forms in a short period of time into a semi rigid shape that has the contours of the ocular socket and is then removed from the socket. This process of obtaining an impression has previously been described by Allen et al. (Allen, L., & Bulgarelli, D. M., "Obtaining and understanding the alginate impression," *The Journal of the American Society of Ocularists*, (19), 4-13 (1988), the entire content of which is herein incorporated by reference).

As those of ordinary skill in the applicable arts will understand, the scope of the invention is not limited in any way by the choice of a scanning device at 320. Non-limiting examples of scanning devices, may include, but are not limited to, a three-dimensional piezo scanning device at 340 or a three-dimensional laser scanning device at 330. These scanning devices create a digital file that is used for three-dimensional computer modeling. The data acquired from the three-dimensional scan are then transferred to a three-dimensional solid modeling or Computer-aided-design/computer-aided-manufacturing (CADCAM) program at 350. It is not uncommon for scan data to include undesirable local shape fluctuations because of uncertainties associated with the scanning process or variations caused by noise in the data acquisition process, such as digitization noise, for example. As such, at step 350, alterations to the shape, which may be necessary in order to provide an optimal fit for the prosthesis, are then made within the three-dimensional modeling software. The resultant shape is then altered within the three-dimensional modeling software in order to provide the individual component shapes that are necessary in order to construct the ocular prosthesis.

Subsequently, the refined shapes are output to a device for fabrication of the components of the ocular prosthesis. It should be understood that the scope of the invention disclosed is not limited to any particular fabrication device, as long as such a device is capable of manufacturing the components of an ocular prosthesis based on scan data from an impression and as long as the raw materials to be used by the chosen devices are acceptable to be used as an ocular prosthesis. As such, an output device is chosen at 360, including, but not limited to, a three-dimensional laser-sintering device at 380, a three-dimensional multi-jet modeling printer, also known as a fused deposition modeling device, at 370, or a subtractive rapid prototyping machine at 390 in order to produce the ocular prosthesis. The result at 395 is a computer scanned, imaged, designed, and fabricated ocular prosthesis body to which an iris and other elements are added and later polished in order to produce the final product.

As illustrated in FIG. 5 at 310, an existing ocular prosthesis can also be reproduced by the disclosed methods. However, if a previous ocular prosthesis is not existent, once the impression is taken of the anophthalmic or enophthalmic socket at 300, a scanning device is selected at 320 and that impression is then reduced to a digital point cloud, polygon, or other three dimensional CADCAM file through the use of a piezo or laser three-dimensional scanning of the impression, as illustrated at 330 and 340 in FIG. 5. As previously explained, the advantageous process of the invention is equally applicable to reproduce an existing prosthesis required to be duplicated, as shown at 310. The computerized image is then modified if necessary at 350 and the resultant data are then sent to a subtractive milling machine at 390 or three-dimensional production processes at 370 and 380, which produces solid three-dimensional parts, such as a selective laser sintering (SLS) machine, which hardens powdered materials by means of a laser into the shape of the part; a stereolithography (SLA) machine which uses a laser beam to cure light sensitive polymers into the shape of the part; a laminated object manufacturing (LOM) device, which uses a laser or other device to cut thin layers of material which are then laminated together; a fused deposition modeling (FDM) device, which extrudes material in layers to build a part; a multi-jet modeling (MJM) printer, which prints thermopolymers in layers that solidify into a solid part; or other digital three-dimensional output devices.

Those of ordinary skill in the applicable arts will understand from the process illustrated in FIG. 5 that the methods of the invention may be implemented in at least three different embodiments. First, the scanning of the impression of the socket or the existing prosthetic shape may be done with a three-dimensional piezo scanning system or with a three-dimensional laser scanner. Secondly, the collection, storage, and manipulation of the data may be done using several different types of CADCAM software programs and storage techniques. Thirdly, the ocular prosthesis may be formed using additive techniques, such as three-dimensional printing and laser sintering, or by subtractive methods of the ocular prosthetic shape, such as subtractive rapid prototyping. Finally, the prosthesis maybe formed using different types of materials that can be generated through these output devices, such as, but not limited to, Poly methyl methacrylate and other millable plastics that can be used in the subtractive process, acrylic photopolymers used in the SLA and MJM processes, thermopolymers used in the FDM process and acrylic powders used in the SLS process.

Figure 6:
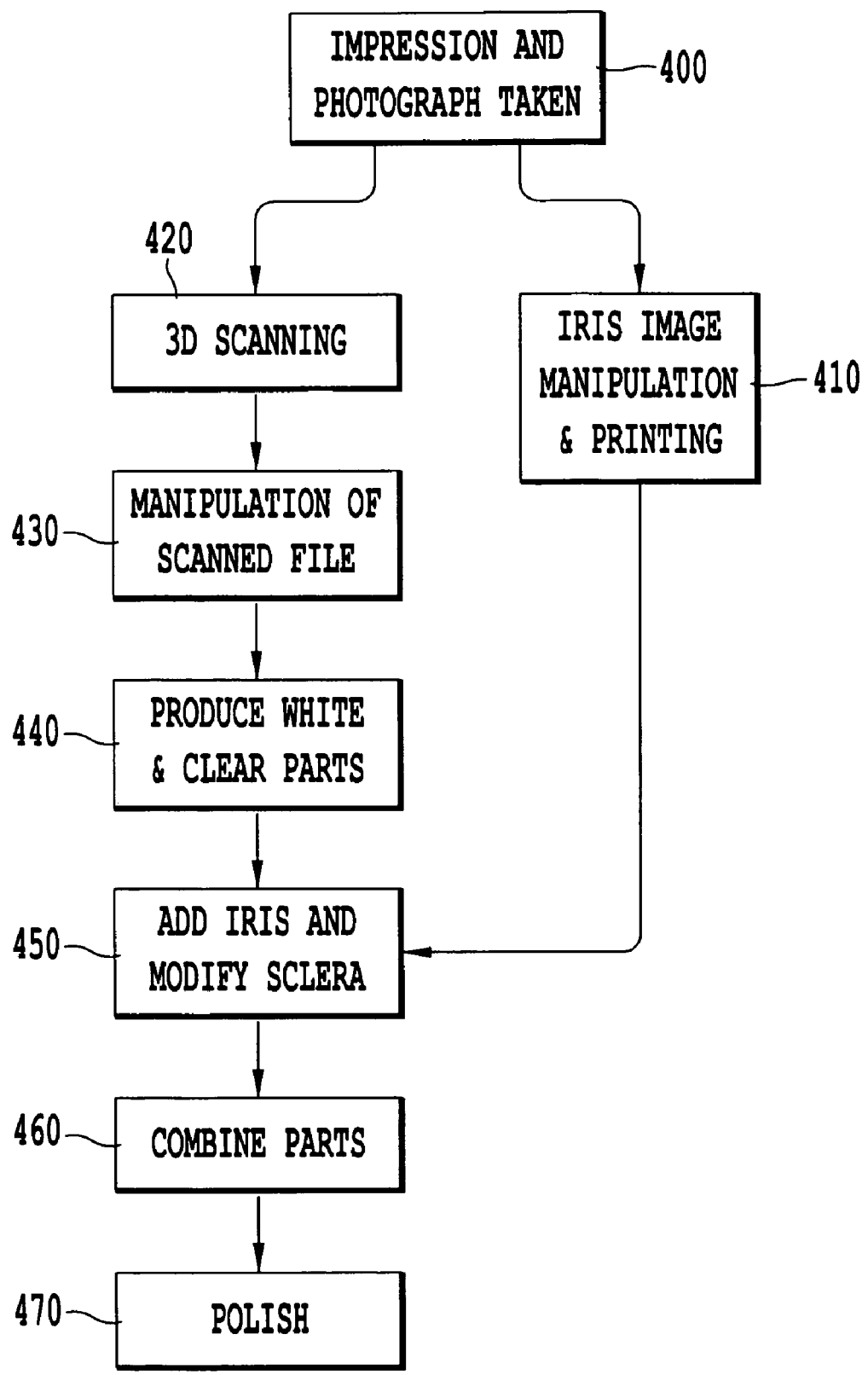
FIG. 6 is a flowchart illustrating a second embodiment for an ocular prosthesis fabrication method according to the invention.

A second embodiment for the ocular prosthesis fabrication method according to the invention, which includes the manipulation and printing of an iris image at 410, is illustrated in FIG. 6. As shown, an impression of the eye socket and at least one photograph of the patient's remaining eye, or a "donor" iris photograph of desirable character in the case of bilaterally blind patients, are first provided at 400. Subsequently, in one hand, the impression or the previous well fitting prosthesis is scanned three dimensionally at 420, the scanned data are manipulated at 430, and the white and clear parts of the prosthesis are machined at 440, and, on the other hand, the photograph of the patient's remaining eye is manipulated and an iris to be disposed on the final ocular prosthesis is then produced at 410. At step 450, the iris produced at 410 is added to the white and clear parts produced at 440; and the sclera is then modified. The parts are then combined at 460 and the final product is polished at 470.

Figure 7:
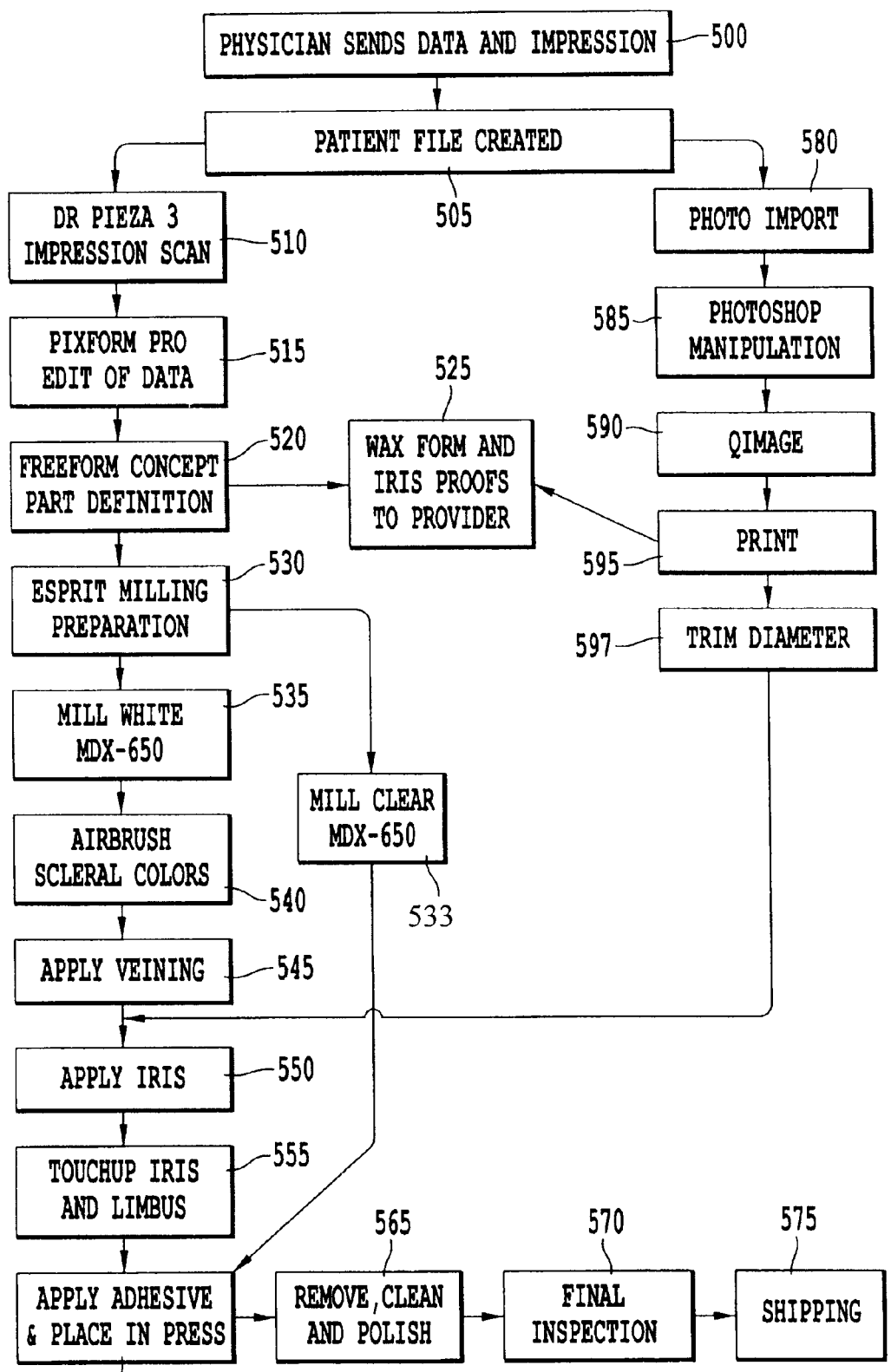
FIG. 7 is a flowchart of the second embodiment of FIG. 6 with additional fabrication steps.

FIG. 7 illustrates a more detailed flowchart of the embodiment of FIG. 6 and FIGS. 8-11 are flowcharts representing additional fabrication steps of various embodiments of the impression scanning process, the scan editing process, the part preparation process, and the iris preparation process, respectively, as further explained below.

As shown at 500 in FIG. 7, the provider first submits photographic data and a socket impression at 500 and a patient file may be created at 505 for management and archival purposes. The impression is then first scanned and edited and a part is defined at steps 510, 515, and 520, while, concurrently, the photographs of the patient's remaining eye are manipulated for the preparation of the iris to be used in the prosthesis by first importing the photograph in a photo editing software program at 580, manipulating that photograph at 585, preparing for printing in a photo manipulating program that arranges the photos for printing, such as Qimage, at 590, and printing the iris at 595. At that time, wax forms created by a three dimensional deposition or other process and iris proofs may be prepared and sent to the physician or provider for any needed adjustments at 525 before the final prosthesis is fabricated. Once the physician or provider approves the proofs, in the case of the subtractive process, the prosthetic component forms are placed in a prepared template in a program, such as Esprit milling software, tool paths are created, and other processes for milling the white and clear components of the prosthesis are prepared at 530, each part is milled at 535 and 533, the milled white component of the prosthesis is then airbrushed with sclera colors at 540, and veins are applied at 545. At this time, the diameter of the iris components are trimmed at 597 and the iris is applied to the white component at 550. Then, the iris and the limbus (i.e., the junction between the iris and the sclera) are touched up at 555 and the clear component milled at 533 is juxtaposed to the white component now containing the iris, scleral modification, and veins, pressed, and light cured at 560. Finally, left over materials are removed and cleaned and the prosthesis is polished at 565 and inspected at 570 before shipping the completed ocular device to the provider at 575.

One of the preferred scanning methods of the impression scan step 510 of FIG. 7 will now be explained with reference to FIG. 8. It should be understood that the scanning process of FIG. 8 is provided as a non-limiting example of a scanning process and those of ordinary skill in the art will understand that such a process may vary according to software and hardware used and still be within the scope of the instant invention.

Figure 8:
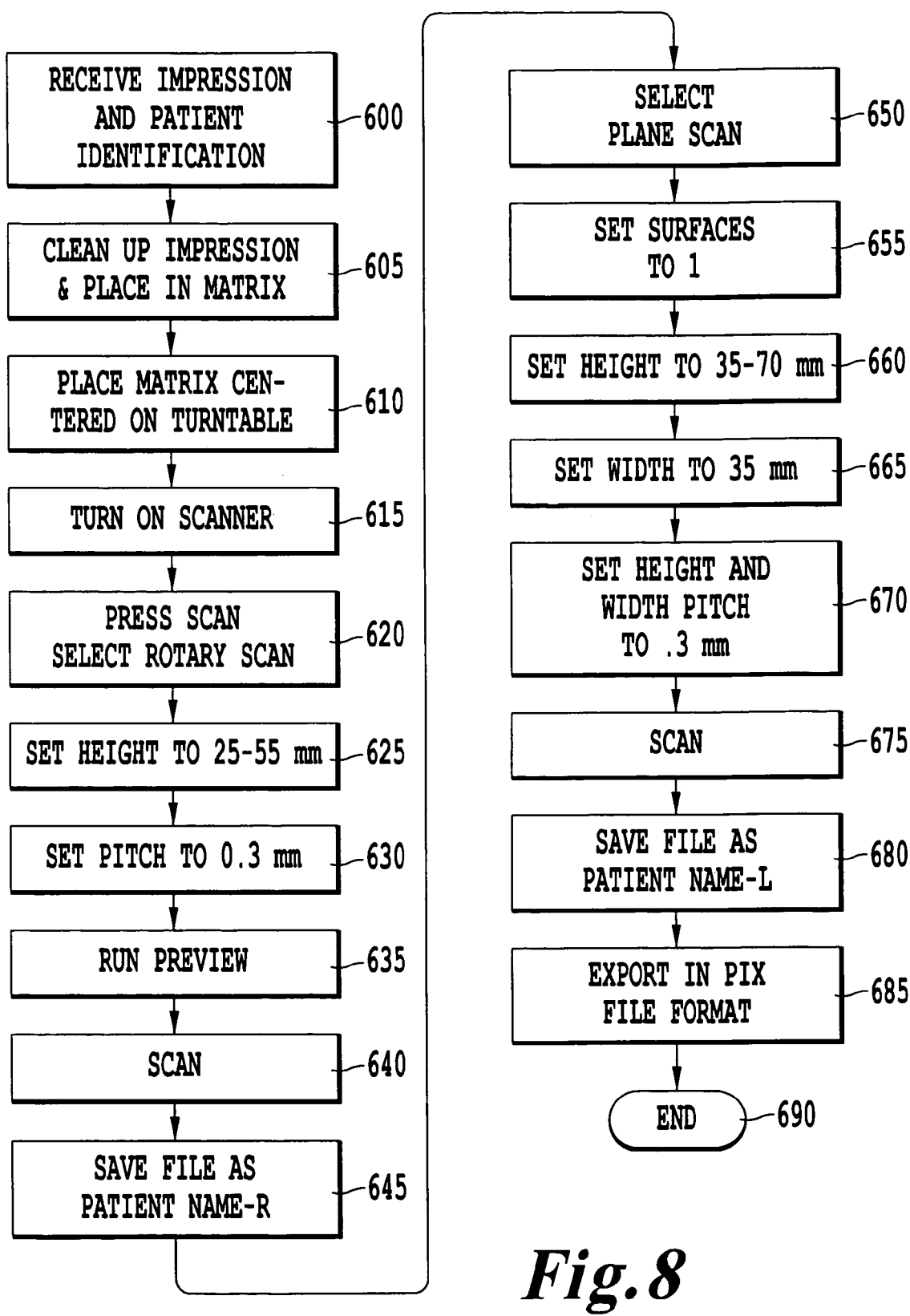
FIG. 8 is a flowchart of the second embodiment of FIGS. 6 and 7 with additional information about one embodiment of an impression scanning process.

As shown in FIG. 8, the impression received from the provider or physician is identified at 600, cleaned at 605, and placed in a turntable receptacle in a scanning device at 610. The scanner is then turned on at 615 and a rotary scan, selected at 620, is first performed, by selecting an appropriate scan height and pitch, running a scan preview, performing the final rotary scan, and saving the scan data at 625, 630, 635, 640, and 645, respectively. Subsequently, the orientation of the impression in the turntable receptacle may be changed and a planar scan is performed as shown at 650. The planar scan includes setting the surface to be scanned, selecting the scan height, scan width, and scan pitch as shown at 655, 660, 665, and 670, respectively, before performing the final scan at 675, saving the planar scan data at 680 and exporting a .pix file at 685 at the end of the impression scan procedure at 690. The settings for the scan are such that the impression is scanned to a degree of accuracy that correlates to the accuracy of the final production output device. The rotational scan records the anterior surfaces of the impression, and the planar scan records the posterior aspect of the impression. As shown in FIG. 8 and just explained, these scans are saved as separate files at 645 and 680. Although other scanners may be used, a high-resolution scanner is preferred, such as the three-dimensional laser scanner (Model LPX-1200) manufactured by Roland.

One of the preferred embodiments of the scan editing process step 515 of FIG. 7 will now be explained with reference to FIG. 9. As previously indicated in the presentation of FIG. 8, it should be understood that the scan editing process of FIG. 9 is provided as a non-limiting example only and those of ordinary skill in the art will understand that such a process may vary according to software and hardware used and still be within the scope of the instant invention.

Figure 9A:
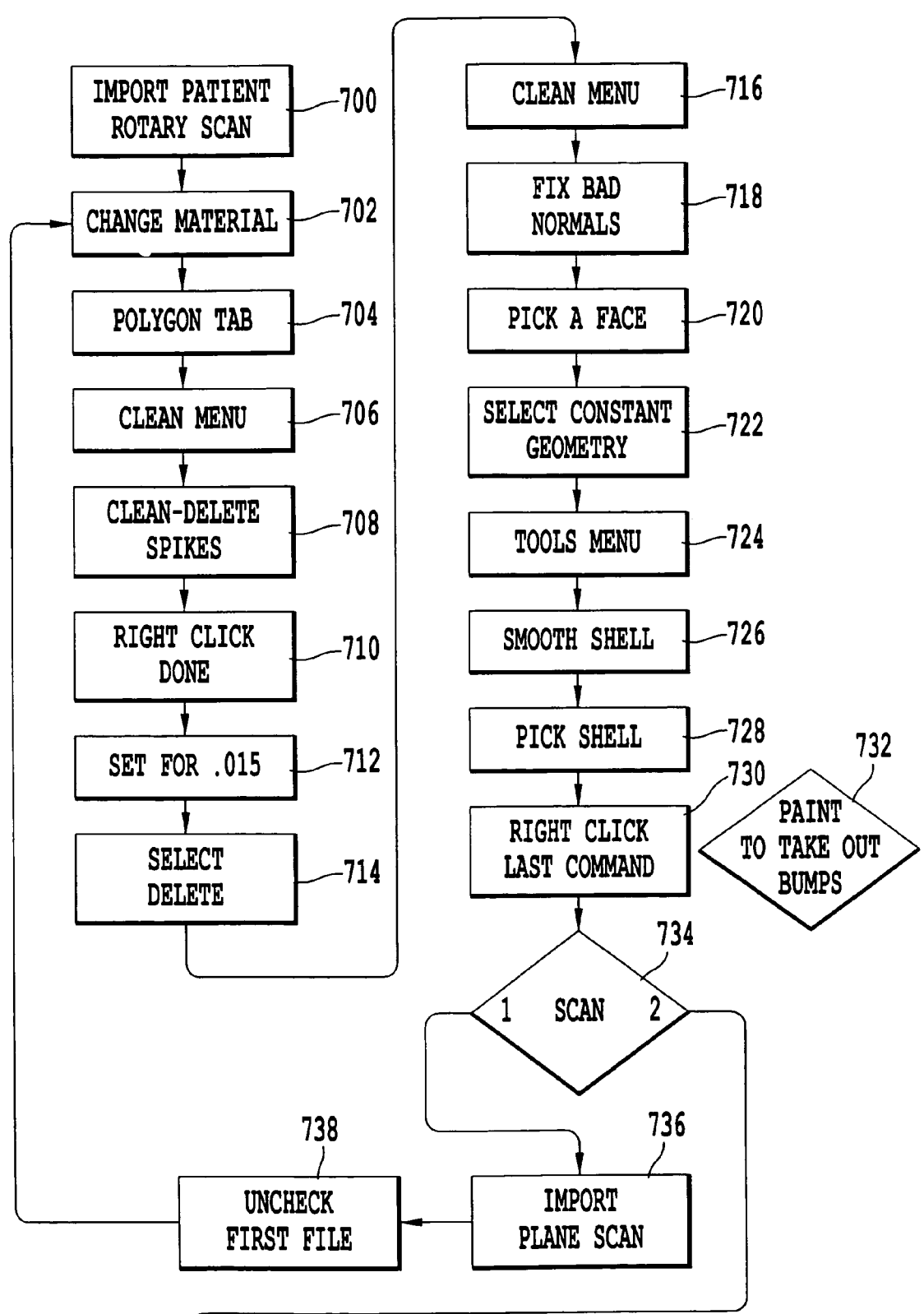
FIGS. 9A and 9B are flowcharts of the second embodiment of FIGS. 6 and 7 with additional information about one embodiment of a scan editing process.
Figure 9B:
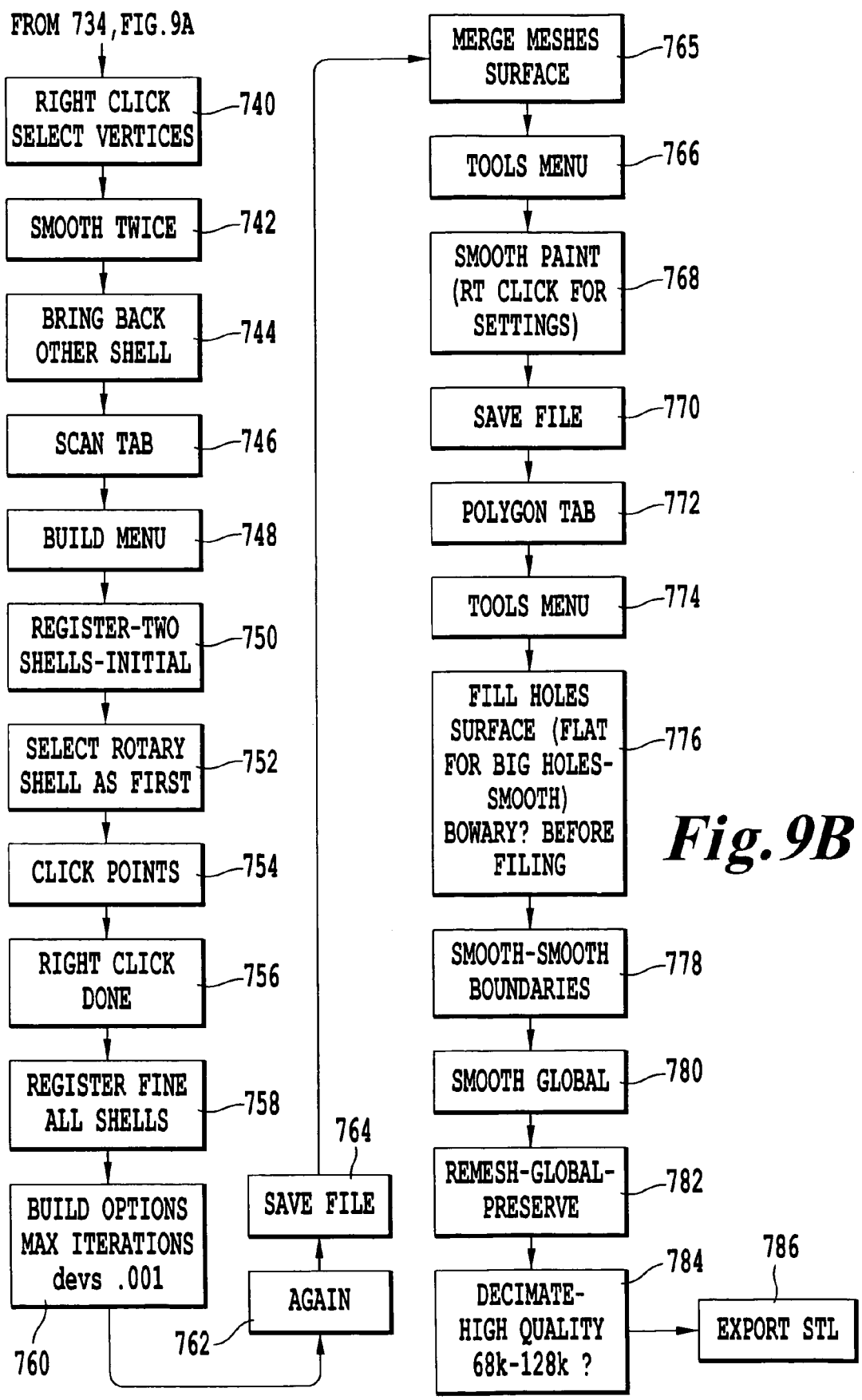

As illustrated in FIG. 9, at the beginning of the scan editing process, the rotary scan file is first imported into a CADCAM program at 700, such as, for example but not as a limitation, Dr. Picza 3 by Roland, and cleaned of aberrations, such as spikes and/or bad normals, and smoothed at the steps 702-732. The planar scan is similarly treated at 734-764 and the cleaned and smoothed rotary and planar scans are then compiled into one complete scan of the impression using a merge function that merges the meshes of the scan file at 765. All holes in the surfaces of the impression file are then filled by the program and the file is prepared for global smoothing, global re-mesh, and a high quality decimation of the final file at 766-784. The file is then exported as an STL file, an industry standard file format in which the object is represented as a logical series of triangles each composed of its normal and three vertices, at 786 for use in the next operation.

Figure 10:
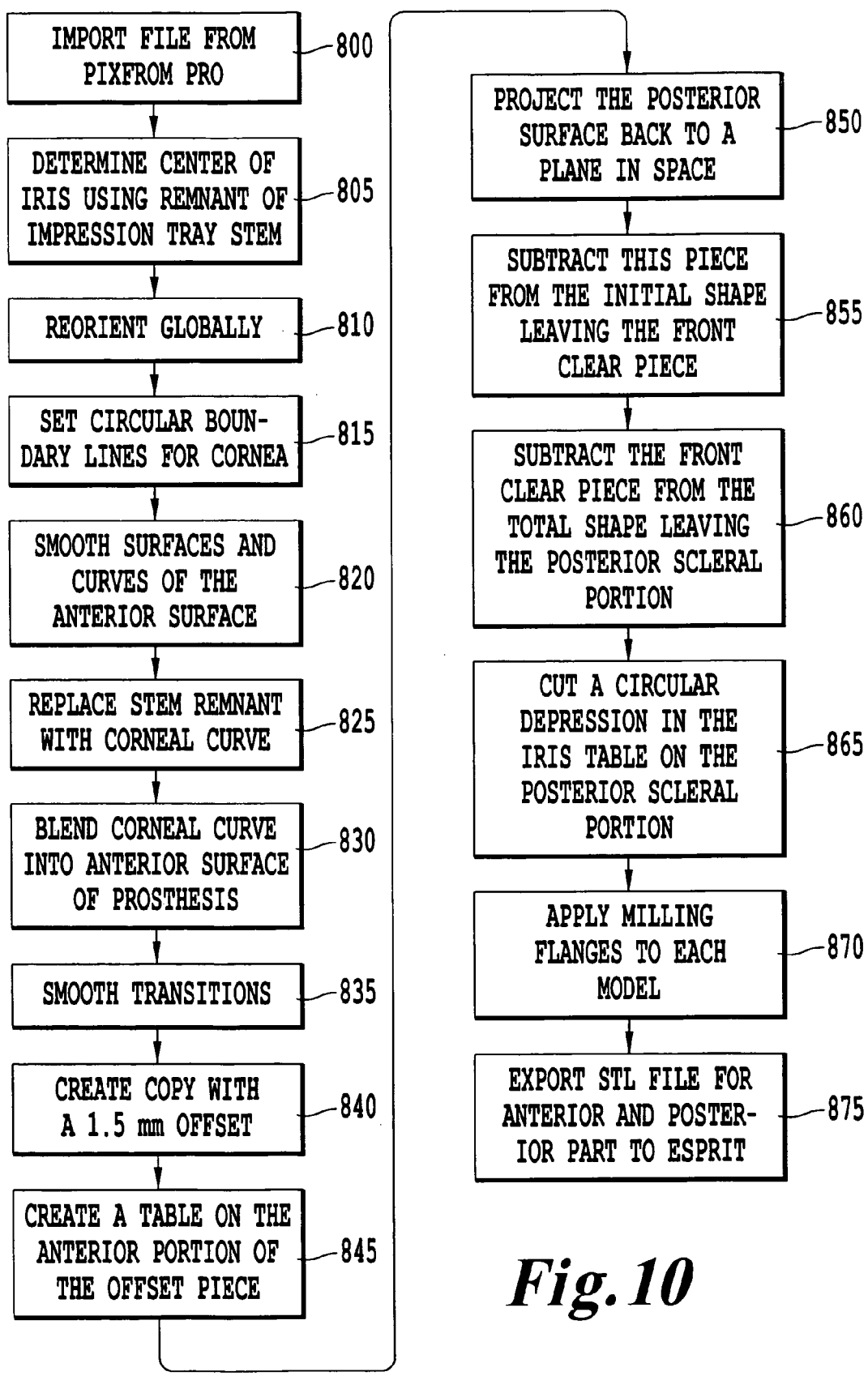
FIG. 10 is a flowchart of the second embodiment of FIGS. 6 and 7 with additional information about one embodiment of a part preparation process.

Preferred embodiments of the process steps 520-545 of FIG. 7 will now be explained with reference to FIG. 10. As previously indicated in the presentation of FIGS. 7-9, it should be understood that the processes to be explained are provided as a non-limiting examples only and those of ordinary skill in the art will understand that such processes may vary according to software and hardware used and still be within the scope of the instant invention.

For these steps in the overall process, a modeling CAD-CAM program, such as Sensible Technologies Freeform Modeling, may be used to modify the prepared impression file into two parts that have the characteristics necessary for manufacture. This process begins with the file being imported into the program and rendered in virtual clay at 800. The object is modified in order assign the center of the iris based upon the central axis of the stem of the impression tray at 805 and then reoriented globally at 810. The circular boundaries of the corneal curve are delineated at 815 and the anterior surfaces and curves of the impression are then smoothed and modified in order to remove any surface irregularities at 820. The artifact created by the stem of the impression tray is then replaced with an anteriorly projecting curve that approximates the anterior surface of a natural cornea at 825 and this corneal curve is then blended and smoothed into the anterior surface of the impression at 830 and 835.

When creating separate anterior and posterior sections of the prosthesis, the object is to divide the revised scan into two parts that have the appropriate geometry for the fabrication process. The first being the clear anterior part and the second being the posterior scleral white portion of the prosthesis. In order to create the form for the anterior clear part, an offset is created from the original shape with a 1.5 mm offset from all of the exterior surfaces at 840. The anterior section of the offset piece is then reduced at the apex of its surface along the previously determined centerline to create a circular table at 845, the circular table later becoming the surface level of the iris. The posterior surfaces of this object are then projected back in space to a plane at 850. This object is then subtracted from the original object at 855 and the resultant shape is the anterior clear shape that will be produced.

In producing the posterior portion of the object, or scleral, a part is created by subtracting the shape of the anterior clear part from the full shape of the object at 860. This posterior portion of the object is then further modified at 865 to allow for a circular depression that is centered upon the iris table and central axis of the iris as previously described. This depression is made to a depth of the thickness of the iris component. Both the anterior and posterior part files are given thin extensions out into a one inch square that allow for stability during the milling process at 870 and these files are then exported as STL files for use in the output machine software at 875.

As shown in step 530 of FIG. 7, each virtual part is then placed into a matrix of one inch wells on a virtual sheet in preparation for milling. This is achieved through the use of a CADCAM program, as for example Esprit 2006, in preparation for the milling process. The tool paths are then created and sent to be milled on a milling machine at 535 and 570. A non-limiting example of such a milling is the Roland MDX-650. The milling machine then mills the parts through a multi-step cutting process that cuts the anterior surface of the prosthesis parts into the appropriate color acrylic using multiple progressively finer bits and then the plastic sheet is turned over and the posterior aspect is milled in a similar manner. These parts are then separated from the sheet of acrylic.

When coloring the scleral colors as indicated in step 540 of FIG. 7, the anterior surface of the posterior scleral part is painted using dry artist pigment mixed with a light cure adhesive, such as Dymax 142-M, to match the colors of the patients corresponding eye. Silk fibers that simulate the veining patterns of the eye are then placed on the anterior surface and coated with the same adhesive to duplicate the patient's natural vein pattern as indicated at step 545 of FIG. 7.

Figure 11:
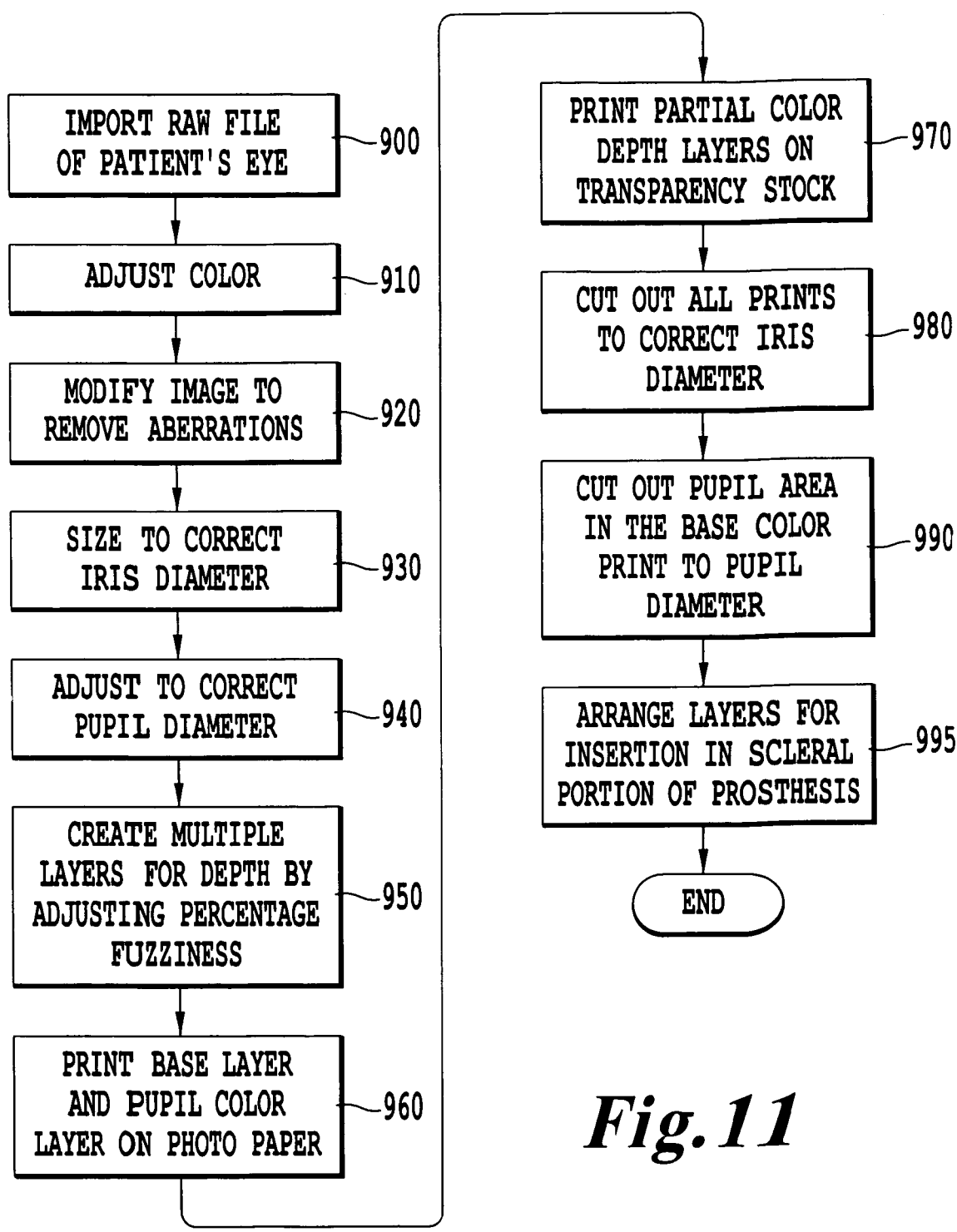
FIG. 11 is a flowchart of the second embodiment of FIGS. 6 and 7 with additional information about one embodiment of an iris preparation process.

One of the preferred embodiments of the iris image manipulation and printing step 410 of FIG. 6 or steps 580-597 of FIG. 7 will now be explained with reference to FIG. 11. As previously indicated in the presentation of FIGS. 7-10, it should be understood that the iris image manipulation and printing process of FIG. 11 is provided as a non-limiting example only and those of ordinary skill in the art will understand that such a process may vary according to software and hardware used and still be within the scope of the instant invention.

Preferably, a high resolution photograph of the patient's remaining eye taken by the provider at the time of the initial impression is imported, in step 900, and modified in an image editing program, such as Adobe Photoshop CS2, in order to create a composite multi-layer photographic iris piece fabricated to match the patient's iris color and diameter. As shown in FIG. 11, this process includes color adjustment, the removal of photographic aberrations, as well as iris diameter, and pupil diameter corrections in steps 910-940. Images of multiple depths are created by adjusting the percentage fuzziness at 950. That is, the iris piece is composed of several layers of photographic prints made with archival quality pigments in a high resolution printer, including a dark almost black pupil layer printed on photographic paper, a base iris color layer printed on photographic paper and cut along the exterior edge of the iris so as to have the appropriate iris diameter, and having a hole of the appropriate diameter for the pupil cut out of the center, as well as several lighter layers of color that have been subtracted out from the base photograph and printed on clear transparency film as shown in steps 960-995. The layers of the iris fabrication are then placed using light cure adhesive into the circular depression that was made in the posterior component of the prosthesis at step 550 of FIG. 7 and the anterior and posterior components of the prosthesis are joined and bonded using a light cured adhesive and an ultraviolet light source as shown in step 560 of FIG. 7. The prosthesis is given a final polish to remove any visible scratches under 10× magnification.

Those of ordinary skill in the applicable arts will appreciate that the above-summarized embodiments of the instant invention are advantageous for several reasons. For example, improved shape accuracy results from the use of both anterior and posterior portions of the initial impression of the ocular socket; (2) allowance for accurate and repeatable shape modification exists due to the accurate machining methods employed. Several fabrication steps are eliminated by providing a way for the retention of a computerized record of an accurate shape of the ocular prosthesis as well as the retention of the photographic files. Materials are used which contain no methyl methacrylate monomer, or that have been tested in a manufacturing facility and proven to contain only acceptably low levels of methyl methacrylate monomer thus possibly reducing the potential for patient allergic reactions. The overall time to produce these advanced ocular prostheses is significantly reduced through the automation of what has in the past been a "hand made" technique, while a more realistic portrayal of a person's natural iris is created.

Recapitulating, an advantageous ocular prosthesis is disclosed, including several embodiments. In a first embodiment, the device includes a posterior sclera portion; an iris disk disposed on a front surface of the posterior sclera portion; and an anterior clear portion covering the front surface of the posterior sclera portion and the iris disk. In this embodiment, the posterior sclera portion includes a recessed table in which the iris disk is disposed and the iris disk includes a plurality of superimposed disks, comprising a dark pupil layer, a base iris color layer, and first and second lighter layers of color. The dark pupil layer is printed on photographic paper; the base iris color layer is printed on photographic paper, is cut along an exterior edge of the iris so as to have an appropriate diameter, and comprises a hole having a diameter equal to a diameter of a pupil. The first and second lighter layers have been subtracted from a base photograph of an iris and printed on a clear transparency film. The posterior sclera portion with the iris disk is adhered to the anterior clear portion with a light cured adhesive and cured with an ultraviolet light source. The posterior sclera portion of this embodiment may also be made hollow and made to include a depression configured to receive a retinal chip configured to be connected to an optic nerve or other neural tissues of a patient. This posterior sclera portion may also include a passage from the depression to a back surface of the posterior sclera portion, the passage being configured to accommodate a cable configured to connect the retinal chip to the optic nerve or other neural tissues. Finally, the iris disk may include a hole from a front surface to a back surface thereof and a light converging lens disposed in the hole, the lens being configured to focus a light incident on the ocular prosthesis on the retinal chip.

In a second embodiment of the invention, the ocular prosthesis includes: a posterior sclera portion and an anterior clear portion, a back surface of the anterior clear portion, being partially nested with a front surface of the posterior sclera portion. The posterior sclera portion is hollow and may be adhered to the anterior clear portion with a light cured adhesive, using an ultraviolet or other light source.

A method of manufacturing the above-described prostheses is also disclosed, including the steps of: providing an impression of an eye socket or an existing ocular prosthesis; scanning the impression or the existing ocular prosthesis; fabricating the posterior scleral portion and the anterior clear portion based on scans produced by the scanning of the impression or the existing ocular prosthesis; and forming the ocular prosthesis by joining the fabricated posterior sclera portion to the anterior clear portion. The fabrication of the posterior sclera portion and the anterior clear portion is based on a CADCAM modification of files generated by the scanning so as to produce manufacturable parts. Polishing the ocular prosthesis may also be necessary in order to remove any scratches generated during the manufacturing process. The scanning processes of an impression or existing ocular prosthesis may include the use of a three-dimensional laser scanner or a three-dimensional piezo scanner to perform a rotary scan of a front surface of the device and a planar scan of a rear surface thereof. In addition, the fabrication further includes printing the posterior sclera portion and the anterior clear portion with a three-dimensional multi-jet modeling printer based on a geometrical model of the posterior and anterior portions generated from the scanning. In addition, sintering the posterior sclera portion and the anterior clear portion may be performed with a three-dimensional laser sintering device based on a geometrical model of the posterior and anterior portions generated from the scanning and milling the posterior sclera portion and the anterior clear portion with a three-dimensional subtractive prototyping machine based on a geometrical model of the posterior and anterior portions generated from the scanning. The fabrication process may further include laminated object manufacturing (LOM) of the posterior sclera portion and the anterior clear portion with a three-dimensional LOM machine based on a geometrical model of the posterior and anterior portions generated from the scanning, fused deposition modeling (FDM) of the posterior sclera portion and the anterior clear portion with a three-dimensional FDM machine based on a geometrical model of the posterior and anterior portions generated from the scanning, stereolithography (SLA) of the posterior sclera portion and the anterior clear portion with a three-dimensional SLA machine based on a geometrical model of the posterior and anterior portions generated from the scanning, or fused deposition modeling of the posterior sclera portion and the anterior clear portion with a three-dimensional subtractive prototyping machine based on a geometrical model of the posterior and anterior portions generated from the scanning. The posterior sclera portion and the anterior clear portion are joined together by a light cured adhesive.

In another embodiment of the invention, fabrication steps include: providing an impression of an eye socket and an iris photograph; scanning the impression of the eye socket; fabricating the posterior sclera portion and the anterior clear portion based on scans produced by the scanning of the impression of the eye socket; forming an iris disk from the iris photograph (as previously described); disposing the iris disk on the fabricated posterior sclera portion; and forming the ocular prosthesis by joining the fabricated posterior sclera portion containing the iris disk to the anterior clear portion. Subsequently, the ocular prosthesis is then polished.

In forming the iris disk, the steps of the fabrication method includes: importing the iris photograph into a photo editing software, adjusting a color of the imported photograph, modifying the imported photograph in order to remove aberrations, sizing the imported photograph to correct iris and pupil diameters, creating multi depth layers by adjusting a percentage fuzziness of the imported photograph, printing a base layer and a pupil color layer on a photo paper, printing partial color depth layers on a transparent medium; cutting out all prints to correct the iris diameter, cutting out a pupil area in the base color print to the pupil diameter, and arranging the layers for insertion in the posterior sclera portion.

Finally, the steps in milling the two portions of the prosthesis include: determining a center of the iris using a remnant of an impression tray stem, reorienting the impression globally, setting circular boundary lines for a cornea, smoothing surfaces and curves of an anterior surface of the prosthesis, replacing the stem remnant with a corneal curve, blending the corneal curve into the anterior surface, smoothing transitions, creating a copy with an offset of 1.5 mm, creating a table on the anterior portion of the offset piece, projecting a posterior surface back to a plane in space, subtracting the projected piece from the initial shape leaving a front clear piece, subtracting the front clear piece from the total shape leaving the posterior scleral portion, cutting a circular depression in the iris table on the posterior scleral portion, applying milling flanges to each model, and exporting a STL file for the anterior and posterior part.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

In addition, while the present invention has been shown in the drawings and fully described above with particularity and detail in connection with what is presently deemed to be practical and several of the preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed is:

1. A method of manufacturing an ocular prosthesis comprising a posterior sclera portion and an anterior clear portion, the method comprising:
   providing an impression of an eye socket or an existing ocular prosthesis;
   scanning the impression or the existing ocular prosthesis to obtain scan data;
   generating a geometrical ocular prosthesis modeling object based on the scan data;
   transforming the geometrical ocular prosthesis modeling object to form a posterior modeling object and an anterior modeling object;
   modifying the posterior modeling object to include an iris table depression for insertion of an iris piece composed of a plurality of layers, the iris table depression including a base surface and a side surface extending from an outer edge of the base surface, at an angle at least substantially perpendicular to the base surface, and continuing to an outer surface of the posterior modeling object, wherein the iris table depression has substantially a same depth as a thickness of the iris piece such that a top surface of the iris piece is formed along a same plane as an edge of the outer surface of the posterior modeling object that is adjacent the iris table depression, wherein each layer of the iris piece is provided adjacent the side surface of the iris table depression such that an entire side surface of each layer is provided substantially a same distance from the side surface of the iris table depression;
   modifying the anterior modeling object to include a substantially level surface;
   fabricating the posterior scleral portion based on the modified posterior modeling object;
   fabricating the anterior clear portion based on the modified anterior modeling object; and
   forming the ocular prosthesis after fabrication of the posterior and anterior portions by joining the fabricated posterior sclera portion to the fabricated anterior clear portion.

2. The method according the claim 1, wherein the fabricating comprises fabricating the posterior sclera portion and the anterior clear portion based on a CADCAM modification of files generated by the scanning so as to produce manufacturable parts.

3. The method according to claim 1, wherein the scanning comprises scanning the impression of the eye socket with a three-dimensional laser scanner.

4. The method according to claim 1, wherein the scanning comprises scanning the existing ocular prosthesis with a three-dimensional laser scanner.

5. The method according to claim 1, wherein the scanning comprises scanning the impression of the eye socket with a three-dimensional piezo scanner.

6. The method according to claim 1, wherein the scanning comprises scanning the existing well fitting prosthesis with a three-dimensional piezo scanner.

7. The method according to claim 1, wherein the scanning comprises a rotary scan of a front surface of the impression and a planar scan of a rear surface of the impression.

8. The method according to claim 1, wherein the fabricating comprises printing the posterior sclera portion and the anterior clear portion with a three-dimensional multi jet modeling printer based, respectively, on the posterior modeling object and the anterior modeling object.

9. The method according to claim 1, wherein the fabricating comprises sintering the posterior sclera portion and the anterior clear portion with a three-dimensional laser sintering device based, respectively, on the posterior modeling object and the anterior modeling object.

10. The method according to claim 1, wherein the fabricating comprises milling the posterior sclera portion and the anterior clear portion with a three-dimensional subtractive prototyping machine based, respectively, on the posterior modeling object and the anterior modeling object.

11. The method according to claim 1, wherein the fabricating comprises laminated object manufacturing (LOM) of the posterior sclera portion and the anterior clear portion with a three-dimensional LOM machine based, respectively, on the posterior modeling object and the anterior modeling object.

12. The method according to claim 1, wherein the fabricating comprises fused deposition modeling (FDM) of the posterior sclera portion and the anterior clear portion with a three-dimensional FDM machine based, respectively, on the posterior modeling object and the anterior modeling object.

13. The method according to claim 1, wherein the fabricating comprises stereolithography (SLA) of the posterior sclera portion and the anterior clear portion with a three-dimensional SLA machine based, respectively, on the posterior modeling object and the anterior modeling object.

14. The method according to claim 1, wherein
the fabricating comprises milling the posterior sclera portion from a first material and milling the anterior clear portion from a second material with a three-dimensional subtractive prototyping machine based, respectively, on the posterior modeling object and the anterior modeling object, and
the second material comprises a transparent material.

15. The method according to claim 1, further comprising:
generating geometrical models of the posterior sclera portion and the anterior clear portion before the fabricating.

16. The method according to claim 15, wherein the generating the geometrical models comprises generating the geometrical models with a CADCAM software.

17. The method according to claim 1, further comprising:
removing undesirable local shape fluctuations from the generated geometrical ocular prosthesis modeling object, before the transforming.

18. The method according to claim 1, further comprising:
altering a shape of the generated geometrical ocular prosthesis modeling object to optimize a fit of the ocular prosthesis, before the transforming.

19. The method according to claim 1, further comprising:
adding a corneal curve to the geometrical ocular prosthesis modeling object and blending the corneal curve into the geometrical ocular prosthesis modeling object, before the transforming.

20. The method according to claim 19, wherein
the corneal curve is added to the geometrical ocular prosthesis modeling object at a position to replace a remnant impression tray stem on the geometrical ocular prosthesis modeling object.

21. The method according to claim 1, wherein the transforming includes copying the geometrical ocular prosthesis modeling object, reducing the size of the copied geometrical ocular prosthesis modeling object with respect to an exterior surface of the geometrical ocular prosthesis modeling object to form the posterior modeling object, and subtracting the posterior modeling object from the geometrical ocular prosthesis modeling object to form the anterior modeling object.

22. The method according to claim 1,
wherein the iris piece layers include a pupil layer printed on photographic paper, and a base iris color layer printed on photographic paper,
and
wherein the plurality of layers includes photographic and transparent paper.

* * * * *